United States Patent [19]

Vecchi

[11] Patent Number: 5,246,702
[45] Date of Patent: Sep. 21, 1993

[54] PROCESS FOR THE PURIFICATION OF COMMERCIAL CARRAGEENINS

[75] Inventor: Giuseppe Vecchi, Aldesago, Switzerland

[73] Assignee: APR Applied Pharma Research S.A., Lugano, Switzerland

[21] Appl. No.: 784,939

[22] Filed: Oct. 31, 1991

[51] Int. Cl.$^5$ ............... A61K 35/78; A61K 35/80
[52] U.S. Cl. ................... 424/195.1; 536/114; 536/127; 536/121; 536/123.1; 424/196.1
[58] Field of Search ............... 424/401, 195.1; 536/114, 127, 1.1

[56] References Cited

U.S. PATENT DOCUMENTS

| | | | |
|---|---|---|---|
| 3,236,833 | 2/1966 | Gordon et al. | 260/209 |
| 4,443,486 | 4/1984 | Guseley | 536/1.1 |
| 4,543,250 | 9/1985 | Witt | 424/70 |
| 5,002,934 | 3/1991 | Norton | 536/114 |

*Primary Examiner*—Thurman K. Page
*Assistant Examiner*—Sally Gardner
*Attorney, Agent, or Firm*—Nixon & Vanderhye

[57] ABSTRACT

Commercial carrageenin is purified to render it suitable for pharmaceutical, dietetic and cosmetic use by treatment with hydrogen peroxide in the presence of a hydrated inert organic solvent.

8 Claims, No Drawings

PROCESS FOR THE PURIFICATION OF COMMERCIAL CARRAGEENINS

The present invention relates to a chemical process for obtaining high purity carregeenins namely copolymers of beta-(1→3)-D-galactose and (1→4)-3,6 anydro-D or L-galactose, partially esterified with sulfuric groups generally salified with the potassium cation.

These copolymers are in fact commonly indicated with the generic name of carrageenins, or carrageenans, or carragens (The Merck Index, 11 Edition).

The carrageenins are obtained through the extraction from the thallus of some red algae present along the coasts of the Atlantic Ocean and have different structural forms respectively indicated as kappa, iota, lambda carrageenin.

The commercial carrageenins generally contain the three forms in variable percentages. The commercial carrageenins contain several impurities such as for example salts, micilages, coloured substances, etc.

They are moreover added with salts, such as for example potassium chloride, or sugars such as for example saccharose, in order to standardize their quality.

Thus the commercial carrageenins are not suitable for those uses requiring a high purity and particularly the absence of substances which may hinder their rational use.

For example the use of the commercial carrageenins in the pharmaceutical field is hindered by the presence of potassium chloride, since it is a salt possessing its own pharmacological properties.

For the dietetic use the presence of saccharose in the commercial carrageenins makes them unuseable for instance in hypocaloric preparations.

For the cosmetic use the presence in the commercial carrageenins of impurities such as coloured substances, mucilages, salts, etc., may involve relevant drawbacks in the formulations.

In all the cases taken into consideration, moreover, both the impurities normally present in the commercial carrageenins, and the added additives, involve relevant risks as regards the compatibility with other compounds present in the formulations and renders particularly complicated the analytical methods required for their identification in the same formulations.

The purpose of the present invention is that of obtaining carrageenins characterized by a high purity and thus particularly suitable for their use in the pharmaceutical, dietetic and cosmetic fields.

This purpose is substantially achieved by the purification process of the present invention which is characterized by hot treating the commercial carrageenins with hydrogen peroxide in the presence of an inorganic inert solvent, miscible with water and suitably hydrated.

Under these conditions the oxidizing action of the hydrogen peroxide acts exclusively on the coloured impurities without altering the chemical structure of the carrageenins which are notoriously sensitive to the oxidating agents; moreover the hydration of the inert organic solvent permits the dissolution and thus the elimination of the water-soluble impurities present in the commercial carrageenins, such as for example sugars and salts. The organic solvent, inert and water miscible, prevents the carrageenin from being swollen owing to the presence of water, which would render fully impossible the treatment cycle.

The concentration of the hydrogen peroxide varies depending on the effect to be obtained; generally this concentration is between 0.1% and 25% with respect to the weight of the carrageenin.

The volume of the mixture consisting of the organic solvent and of the water may vary within wide limits and, owing to practical reasons connected to the process, is at least two times by volume the weight of the carrageenin to be purified; more preferably is about five times.

The hydration rate of the organic solvent is between 5% and 50% v/v and is preferably 25%.

The reaction temperature depends on the organic solvent which is used and is preferably between 60° C. and 120° C. in order to accelerate the purification process.

The organic solvent, inert and water miscible, can be for example ethanol, isopropanol, methanol, acetone, dimethylformamide, acetonitrile and the like; it is preferably a lower aliphatic alcohol.

The carrageenins obtained by the purification process of the present invention owing to their high purity are particularly suitable for use in the pharmaceutical, dietetic and cosmetic fields.

Use in the Pharmaceutical Field

The carrageenins of the present invention can be used in the pharmaceutical field for their thickening and gelifying properties.

The pharmaceutical forms in which these carrageenins are used are all those known in the art and particularly syrups, suspensions, unit doose envelopes, tablets, gels for topical use, collyria, nose drops, etc.

Use in the Dietetical Field

The high purity of the carrageenins of the present invention and their intrinsic properties as gelifiers, suspenders, thickeners, stabilizers make them particularly suitable for those dietetical formulations in which the presence of water is required, such as for example jellies, fruit jellies, desserts, etc.

Also for the extemporary preparations to be dispersed in water for the administration the claimed carrageenins are useful.

Moreover in the dietical field the carrageenins obtained by the process of the present invention can be used alone as satiating preparations; for this purpose they can be accompanied by complementary substances such as vetal fibers, mineral salts, etc.

Use in the Cosmetic Field

In this field the carrageenins of the present invention can be advantageously used owing to their peculiar properties and to their high purity in all those formulations known in the art in which it is necessary to enhance particular characteristics such as the limpidity, the absence of foreign colours, a high hydration degree, etc.

Examples of these formulations include gel creams, lotions, hair care gummy preparations, gum hygiene gels, gel formulations for the intimate hygiene, etc.

The following non-limiting examples illustrate the invention. More particularly example 1 illustrates the process of the invention, whereas the examples 2–23 relate to compositions prepared with the carrageenin obtained by the process of example 1.

EXAMPLE 1

Purification Process 100 g of commercial carrageenin, having the following analytical characteristics: hazel-brown coloured powder; sulfates (as sodium sulfate) 4.25%; chlorides (as potassium chloride) 6.63%; sugras (as saccharose) 10%; foreign mucilages 3%; are suspended in a mixture comprising 375 ml of 95° ethanol and 125 ml of a 4% water solution of hydrogen peroxide.

The stirred mixture is brought to the refluxing temperature of 93° C. and refluxed for four hours.

After complete decolouration the white suspension is filtered and washed on the filter portionwise with a mixture consisting of 95° ethanol (375 ml) and distilled water (125 ml).

A last washing with 95° ethanol (60 ml) is effected.

After drying in an oven under vacuum up to constant weight an absolutely white product is obtained having the following analytical properties: sulfates (as sodium sulfate) 52 ppm; chlorides (as potassium chloride) 0.17%; sugars absent; foreign mucilages absent.

The weight yield is 75%.

EXAMPLE 2

Polyvitaminic Syrup 100 g contain:

active principle: thiamine hydrochloride 9 mg, riboflavin 6 mg, pyridoxine chloridrate 4 mg, nicotinamide 110 mg, calcium pantothenate 6 mg, p-aminobenzoic acid 3 mg, choline chloride 130 mg, cyanocobalamine 80 mg, inositol 10 mg excipients: purified carrageenin of Example 1 1 g, sodium benzoate 0,100 g, glycerol 15 g, saccharin sodium 0,070 g, cetyltrimethylammonium p-toluenesulphonate 0,022 g, vanilline 0,025 g, depurated water enough to 100 g.

EXAMPLE 3

Antilepemic Composition in One Dose Envelopes

One envelope contains:

Active principle Deae-dextran 1.5 g

Excipients: purified carrageenin of example 1 0.5 g, Acesulfame 0,070 g, sorbitol 1 g, Tropical natural flavouring powder 0.070 g, cyder natural flavouring powder 0,030 g, citric acid 0,100 g, riboflavine 5-phosphate 0,002 g

EXAMPLE 4

Antilipemic Composition in Form of Gelatin for Multidose Administration 100 g of composition contain:

Active principle: Daea-dextran 10 g

Excipients: purified carrageenin of ex. 1 3 g, potassium sorbate 0,2 g, citric acid 1 g, manadarin flavour 1 ml, sorbitol 20 g, aspartame 0,100 g, depurated water enough to 100 g.

EXAMPLE 5

Antiulcer Composition in One Dose Envelopes

One envelope contains:

Active principle: sucralfate 0,5 g,

Excipients: purified carrageenin of ex.1 0,5 g, acesulfame 0,020 g, aspartame 0,030 g, mint flavouring powder 0,030 g, tropical flavouring powder 0,020 g.

EXAMPLE 6

Antiulcer Composition in Multidose Suspension 100 g of suspension contain:

Active principle: sucralfate 10 g

Excipients: purified carrageenin of ex.1 2 g, saccharin sodium 0,070 g, mint flavouring powder 0,100 g, tropical flavouring powder 0,050 g, sodium benzoate 0,200 g, depurated water enough to 100 g.

EXAMPLE 7

Antiacid Composition in One Dose Envelopes

One envelope contains:

Active principle: magnesium hydroxide 0,400 g, aluminium hydroxide as dry gel 0,400 g, Excipients: purified carrageenin of ex.1 0,4 g, aspartame 0,040 g, licorice flavouring powder 0,100 g, mint flavouring powder 0,030 g,

EXAMPLE 8

Antiacid Composition in Extemporary Multidose Suspension Form 100 ml of suspension contain:

Active principle: magnesium hydroxide 6 g, aluminium hydroxide as dry gel 12 g,

Excipients: purified carrageenin of ex.1 3 g, sodium benzoate 0,100 g, saccharin sodium 0,070 g, acesulfame 0,030 g, vanilla flavouring powder 0,070 g, banana flavouring powder 0,030 g.

EXAMPLE 9

Antiacid Composition in Form of Masticable Tablets

One tablet contains:

Active principle: magnesium hydroxide 0,3 g, aluminium hydroxide as dry gel 0,6 g, Excipients: purified carrageenin of ex.1 0,100 g, lactose 0,100 g, mint flavouring powder 0,010 g, licorice flavouring powder 0,020 g, aspartame 0,020 g.

EXAMPLE 10

Antiinflammatory Gel Composition for Topical Use 100 g topical gel contain

Active principle: ibuprofen lysine salt 10 g,

Excipients: purified carrageenin of ex.1 2 g, maltol 10 g, glycerol 5 g, lavender perfume (enough), methylparaben, 0,170 g, propilparaben 0,060 g, preserved water enough to 100 g.

EXAMPLE 11

Collyrium 100 ml contain:

Active principle: dexamethasone-21 disodium phosphate 0,150 g, neomycine sulfate 0,500 g, gramycidine 0,005 g, tetryzolinehydrochloride 0,100 g, Excipients: purified carrageenin of ex.1 0,200 g, sodium chloride, 0,600 g, sodium thiomersal 0,010 g, sterile distilled water enough to 100 ml.

EXAMPLE 12

Octologigal Drops 100 ml contain

Active principle: polymyxin B sulfate 1.000.000 U, Neomycine sulfate 340.000 U, hydrocortisone disodium hemisuccinate 20 mg, Excipients: purified carrageenin of ex.1 0,200 g, glycerol 5 g, sterile distilled water 100 ml.

EXAMPLE 13

Rhinological Drops 100 ml contain:

Active principle: sodium chromoglicate 4 g, chlorphenamine maleate 0,2 g.

Excipients: purified carrageenin of ex.1 0,2 g, sodium thiomersal 0,010 g, sterile distilled water enough to 100 ml.

EXAMPLE 14

Satiating Fruit Type Jellies for Dietetic Use 100 g contain:

purified carrageenin of ex.1 3 g, potassium sorbate 0,2 g, fructose 7 g, sorbitol 2.75 g, aspartame 0,2 g, citric acid 50% solution 2 ml, E 124 0,005 g, Blueberry natural flavour 1 ml, depurated water enough to 100 g.

EXAMPLE 15

Jam Type Jelly for Dietetic Use

Purified carrageenin of ex.1 1,5 g, potassium sorbate 0,2 g, fructose 7 g, sorbitol 2,75 g, aspartame 0,2 g, citric acid 50% solution 2 ml, sodium, riboflavine 5-phosphate 0,005 g, mandarin natural flavour 1 ml, depurated water enough to 100 g.

EXAMPLE 16

Hypocalori Milk Dessert for Dietetic Use

Purified carrageenin of ex.1 1,5 g, potassium sorbate 0,2 g, fructose 7 g, sorbitol 2,75 g, aspartame 0,2 g, powdered milk 50 g, vanilla flavour 0,050 g, depurated water enough to 100 g

EXAMPLE 17

Satiating Composition as One Dose Envelopes

One envelope contains:

Purified carrageenin of ex.1 0,5 g, aspartame, 0,100 g, citric acid 0,100 g, sodium riboflavine 5-phosphate 0,005 g, tropical flavouring powder 0,050 g

EXAMPLE 18

Gengival Gel 100 g contain:

Active principle: 1% native collagen 10 g,

Excipients: purified carrageenin of ex.1 0,5 g, CMC 2 g, 70% sorbitol 9 g, mint 0,150 g, preserved water enough to 100 g

EXAMPLE 19

Gengival Gel g 100 contain the same compounds of ex. 18 and 1% of camomile soft extract.

EXAMPLE 20

Gengival Gel g 100 contain the same compounds of ex. 18 and 0,5% of allantoin.

EXAMPLE 21

Fluid Gel for Female Intimate Hygiene g 100 contain:

sodium hyaluronic acid salt 0,5 g, purified carrageenin of ex.1 0,25 g, water-soluble rose perfume 0,5 g, preserved water enough to 100 g.

EXAMPLE 22

Fluid Gel for Female Intimate Hygiene g 100 contain the same compounds of ex.21 and 0,5% of allantoin.

EXAMPLE 23

Fluid Gel for Female Intimate Hygiene g 100 contain the same compounds of Ex. 21 and 5% of glycole extract of Centella asiatica.

I claim:

1. Process for the purification of carrageenin, comprising the steps of:
   heating at a temperature of from 60° C. to 120° C. a mixture comprising carrageenin to be purified, hydrogen peroxide and a hydrated inert organic water miscilbe solvent, said solvent being present to avoid altering the chemical structure of the carrageenin; and
   separating the purified carrageenin.

2. Process according to claim 1, wherein said inert organic solvent is selected from the group consisting of methanol, ethanol, isopropanol, acetone, dimethylformamide and acetonitrile.

3. Process according to claim 1, wherein said inert organic solvent is a lower aliphatic alcohol containing 1 to 4 carbon atoms.

4. Process according to claim 1, wherein said organic solvent is hydrated to the extent of 5% to 50% v/v.

5. Process according to claim 1, wherein said organic solvent is hydrated to the extent of 25% v/v.

6. Process according to claim 1, wherein said volume of the hydrated inert organic solvent is equal to at least twice the volume of the carrageenin to be purified.

7. Process according to claim 6, wherein said volume of the hydrated inert organic solvent is equal to 5 times the volume of the carrageenin to be purified.

8. Process according to claim 1, wherein the hydrogen peroxide is present in an amount between 0.1 to 25% by weight based on the weight of the carrageenin to be purified.

* * * * *